United States Patent
Khan et al.

(10) Patent No.: US 6,800,488 B2
(45) Date of Patent: Oct. 5, 2004

(54) METHODS OF MANUFACTURING REAGENT TEST STRIPS

(75) Inventors: Tahir Sadik Khan, San Jose, CA (US); Yeung Siu Yu, Pleasanton, CA (US); Edward G. Rice, Palo Alto, CA (US)

(73) Assignee: LifeScan, Inc., Milpitas, CA (US)

( * ) Notice: Subject to any disclaimer, the term of this patent is extended or adjusted under 35 U.S.C. 154(b) by 26 days.

(21) Appl. No.: 09/737,179

(22) Filed: Dec. 13, 2000

(65) Prior Publication Data

US 2002/0072124 A1 Jun. 13, 2002

(51) Int. Cl.[7] .............................................. G01N 21/75
(52) U.S. Cl. .................. 436/166; 436/169; 436/170; 422/58
(58) Field of Search .............................. 422/56, 58, 61; 436/164, 169, 170, 95, 166

(56) References Cited

U.S. PATENT DOCUMENTS

| | | | |
|---|---|---|---|
| 962,333 A | * | 6/1910 | Foster .......................... 384/555 |
| 4,067,492 A | * | 1/1978 | Gargan .................. 229/120.25 |
| 4,637,403 A | * | 1/1987 | Garcia et al. ............... 600/583 |
| 4,883,764 A | | 11/1989 | Kloepfer |
| 5,032,703 A | * | 7/1991 | Henschen et al. ....... 219/85.22 |
| 5,059,394 A | | 10/1991 | Phillips et al. |
| 5,067,309 A | | 11/1991 | Carlberg et al. |
| 5,179,005 A | | 1/1993 | Phillips et al. |
| 5,418,142 A | | 5/1995 | Kiser et al. |
| 5,462,032 A | | 10/1995 | Nakamura |
| 5,547,702 A | | 8/1996 | Gleisner |
| 5,563,042 A | | 10/1996 | Phillips et al. |
| 5,605,837 A | | 2/1997 | Karimi et al. |
| 5,620,863 A | | 4/1997 | Tomasco et al. |
| 5,753,452 A | | 5/1998 | Smith |
| 5,789,255 A | | 8/1998 | Yu |
| 5,843,691 A | | 12/1998 | Douglas et al. |
| 5,968,836 A | | 10/1999 | Matzinger et al. |
| 5,972,294 A | | 10/1999 | Smith et al. |

FOREIGN PATENT DOCUMENTS

| | | |
|---|---|---|
| DE | 19938479 A | 2/2000 |
| EP | 0949002 A | 10/1999 |
| WO | WO 97/38126 A | 10/1997 |

* cited by examiner

Primary Examiner—Lyle A. Alexander
(74) Attorney, Agent, or Firm—Susan C. Tall; Bozicevic, Field & Francis, LLP

(57) ABSTRACT

Methods for making reagent test strips are provided. In the subject methods, a test strip precursor made up of an elongated support material having a planar surface and a narrow stripe of reagent material positioned along its central axis is cut according to an inter-digitating pattern to produce the plurality of reagent test strips. The initial precursor material may be a tape or in the form of a card. Also provided are the reagent test strips produced by the subject methods and kits that include the same. The subject reagent test strips and kits find use in analyte detection and/or concentration determination assays.

23 Claims, 8 Drawing Sheets

METHODS OF MANUFACTURING REAGENT TEST STRIPS

INTRODUCTION

1. Field of Invention

The field of this invention is analyte determination, and is particularly directed to reagent test strips for use in analyte determination assays.

2. Background of the Invention

Analyte detection in physiological fluids, e.g., blood or blood-derived products, is of ever increasing importance to today's society. Analyte detection assays find use in a variety of applications, including clinical laboratory testing, home testing, etc., where the results of such testing play a prominent role in the diagnosis and management of a variety of conditions. The more common analytes include glucose, alcohol, formaldehyde, L-glutamic acid, glycerol, galactose, glycated proteins, creatinine, ketone body, ascorbic acid, lactic acid, leucine, malic acid, pyruvic acid, uric acid and steroids, etc. In response to this growing importance of analyte detection, a variety of analyte detection protocols and devices for both clinical and home use have been developed.

Many current analyte detection protocols employ a reagent test strip to detect an analyte in a sample. With reagent test strips, a sample is applied to a reagent area of a small strip and a signal is produced that is indicative of the presence of analyte in the sample. As the demand for such test strips has grown, the need for ever more efficient test strip manufacturing protocols that minimize the waste of expensive materials has increased.

As such, there is continued interest in the development of new manufacturing methods that would increase the efficiency of manufacturing reagent test strips. Of particular interest would be manufacturing methods that provide for increased manufacturing efficiency, reduced cost and are amenable to continuous manufacture procedures.

Relevant Literature

U.S. Patents of interest include: U.S. Pat. No. 5,067,309. Also of interest are U.S. Pat. Nos. 5,972,294; 5,968,836; 5,843,691; 5,789,255; 5,753,452; 5,620,863; 5,605,837; 5,563,042; 5,462,032; 5,418,142; 5,059,394; 5,179,005.

SUMMARY OF THE INVENTION

Methods for making reagent test strips are provided. In the subject methods, a test strip precursor made up of an elongated support material having a planar surface and a narrow strip of reagent material positioned along its central axis is cut according to an inter-digitating pattern to produce the plurality of reagent test strips. The initial precursor material may be a tape or in the form of a card or analogous shape. Also provided are the reagent test strips produced by the subject methods and kits that include the same. The subject reagent test strips and kits find use in analyte detection and/or concentration determination assays.

DESCRIPTION OF THE SPECIFIC EMBODIMENTS

Figure 1:
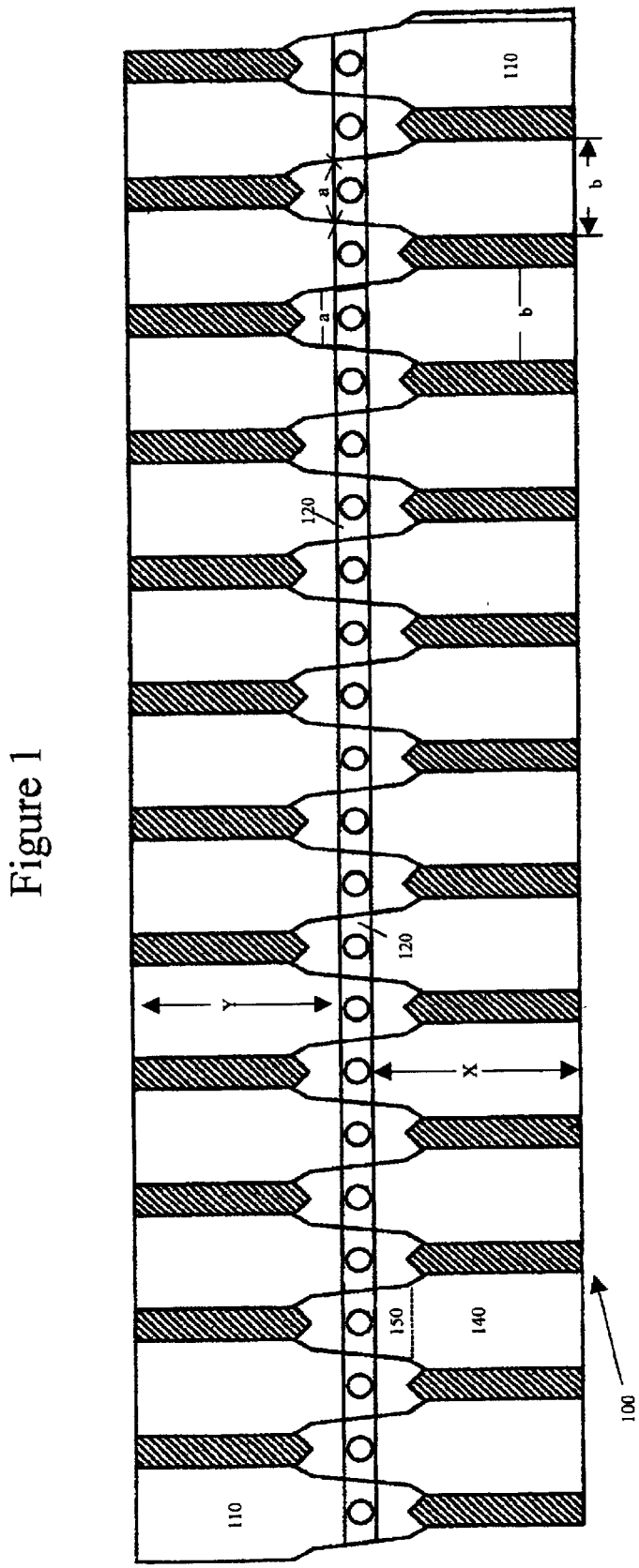
FIG. 1 provides a top view illustration of a test strip precursor with an inter-digitating pattern superimposed thereon.

Methods for making reagent test strips are provided. In the subject methods, a test strip precursor made up of an elongated support material having a planar surface and a narrow strip of reagent material positioned along its central axis is cut according to an inter-digitating pattern to produce the plurality of reagent test strips. The initial precursor material may be a tape or in the form of a card or analogous shape. Also provided are the reagent test strips produced by the subject methods and kits that include the same. The subject reagent test strips and kits find use in analyte detection and/or concentration determination assays. In further describing the invention, the subject methods of manufacture are described first, followed by a description of exemplary embodiments of reagent test strips produced by the methods, representative applications of use of the reagent test strips, and kits that include the subject reagent test strips.

Before the subject invention is described further, it is to be understood that the invention is not limited to the particular embodiments of the invention described below, as variations of the particular embodiments may be made and still fall within the scope of the appended claims. It is also to be understood that the terminology employed in this description is for the purpose of describing particular embodiments, and is not intended to be limiting. Instead, the scope of the present invention will be established by the appended claims.

In this specification and appended claims, singular references include the plural, unless the context clearly dictates otherwise. Unless defined otherwise, all technical and scientific terms used herein have the same meaning as commonly understood to one of ordinary skill in the art to which this invention belongs.

Methods of Manufacture

As summarized above, the present invention provides methods of manufacturing reagent test strips. By reagent test strip is meant an article of manufacture that includes a support material and a reagent material, where the strip includes at least two domains, a handling domain and a sample application domain, where the reagent material is present only in the sample application domain. Exemplary reagent test strips that may be produced using the subject methods are described in greater detail, infra.

In the subject methods, the first step is to provide a test strip precursor. By test strip precursor is meant an elongated support material having a first planar surface and a narrow stripe of reagent material positioned on the central axis of the first planar surface. The test strip precursor may be in the form of a continuous tape or be in the form of a card, e.g., a parallelogram or analogous shape, of shorter length. As such, the length of the test strip precursor may vary considerably, depending on whether it is in the form of a tape or has a shorter shape, e.g., is in the form of a card. The width of the test strip precursor may also vary depending on the nature of the particular test strip being manufactured. In general the width of the test strip precursor may range from about 0.80 to 4.0 inches, usually from about 1.20 to 3.0 inches and more usually from about 1.6 to 2.8 inches; where in certain embodiments the width of the test strip precursor may range from about 2.40 to 4.0 inches, usually from about 2.5 to 3.2 and more usually from about 2.6 to 2.8 and in other embodiments the width of the test strip precursor may range from about 0.8 to 3.0, usually from about 1.2 to 2.5 inches and more usually from about 1.5 to 2.0 inches.

As mentioned above, the test strip precursor is made up of an elongated support material that has a narrow reagent strip positioned on a planar surface of the inert support material. As such, the elongated support material has dimensions that are the same as the dimensions of the test strip precursor in terms of length and width, as described above. The solid support component of the test strip blank provides physical form and rigidity to the strip, among other features. The solid support of the test strip blank may be fabricated from a variety of materials, where suitable materials that may be employed as the substrate include plastics, e.g. PET, PETG, polyimide, polycarbonate, polystyrene, nylon, silicon, ceramic, glass, and the like; paper, plastic paper laminate, metallic sheets or any other suitable material, including a composite material of a support coated with a metallic and/or conductive coating which acts as an electrode (such as palladium, gold, platinum, silver, iridium, carbon (conductive carbon ink), doped tin oxide, stainless steel, e.g., where the strip is an electrochemical test strip. For examples of support materials that find use in certain embodiments of the subject invention, see e.g., the support materials disclosed in U.S. Pat. Nos. 4,935,346 and 5,304, 468, the disclosures of which are herein incorporated by reference.

Positioned on one of the planar surfaces of the elongated support material, e.g., the top or bottom surface depending on the particular vantage point, is a narrow strip of reagent material. The narrow stripe of reagent material is generally positioned along the central longitudinal axis of the elongated support material. By central longitudinal axis is meant the center axis that is equidistant from each side of the support material. Generally, the two sides of the narrow reagent stripe are equidistant from the corresponding adjacent edge of the elongated support material.

The reagent material that is present in the narrow reagent stripe of the reagent strip precursor includes one or more specific reagent members of a signal producing system. By signal producing system is meant one or more reagents which work in combination to provide a detectable signal in the presence of an analyte that can be used to determine the presence and/or concentration of analyte. The signal producing system may be a signal producing system that produces a color that can be related to the presence or concentration of an analyte or it may be a signal producing system that produces an electrical current that can be related to the presence or concentration of an analyte. As such, the signal producing system may be a color producing system or a current producing system.

A variety of different color signal producing systems are known. Representative color signal producing systems of interest include analyte oxidation signal producing systems. By analyte oxidation signal producing system is meant that in generating the detectable colorimetric signal from which the analyte concentration in the sample is derived, the analyte is oxidized by a suitable enzyme to produce an oxidized form of the analyte and a corresponding or proportional amount of hydrogen peroxide. The hydrogen peroxide is then employed, in turn, to generate the detectable product from one or more indicator compounds, where the amount of detectable product produced by the signal producing system, i.e. the signal, is then related to the amount of analyte in the initial sample. As such, the analyte oxidation signal producing systems present in the subject test strips are also correctly characterized as hydrogen peroxide based signal producing systems.

As indicated above, the hydrogen peroxide based signal producing systems include an enzyme that oxidizes the analyte and produces a corresponding amount of hydrogen peroxide, where by corresponding amount is meant that the amount of hydrogen peroxide that is produced is proportional to the amount of analyte present in the sample. The specific nature of this first enzyme necessarily depends on the nature of the analyte being assayed but is generally an oxidase. As such, the first enzyme may be: glucose oxidase (where the analyte is glucose); cholesterol oxidase (where the analyte is cholesterol); alcohol oxidase (where the analyte is alcohol); lactate oxidase (where the analyte is lactate) and the like. Other oxidizing enzymes for use with these and other analytes of interest are known to those of skill in the art and may also be employed. In those embodiments where the reagent test strip is designed for the detection of glucose concentration, the first enzyme is glucose oxidase. The glucose oxidase may be obtained from any convenient source, e.g., a naturally occurring source such as *Aspergillus niger* or Penicillum, or recombinantly produced.

The second enzyme of the signal producing system is an enzyme that catalyzes the conversion of one or more indicator compounds into a detectable product in the presence of hydrogen peroxide, where the amount of detectable product that is produced by this reaction is proportional to the amount of hydrogen peroxide that is present. This second enzyme is generally a peroxidase, where suitable peroxidases include: horseradish peroxidase (HRP), soy peroxidase, recombinantly produced peroxidase and synthetic analogs having peroxidative activity and the like. See e.g., Y. Ci, F. Wang; Analytica Chimica Acta, 233 (1990), 299–302.

The indicator compound or compounds, e.g. substrates, are ones that are either formed or decomposed by the hydrogen peroxide in the presence of the peroxidase to produce an indicator dye that absorbs light in a predetermined wavelength range. Preferably the indicator dye absorbs strongly at a wavelength different from that at which the sample or the testing reagent absorbs strongly. The oxidized form of the indicator may be the colored, faintly-colored, or colorless final product that evidences a change in color. That is to say, the testing reagent can indicate the presence of analyte, e.g., glucose, in a sample by a colored area being bleached or, alternatively, by a colorless area developing color.

Indicator compounds that are useful in the present invention include both one-and two-component colorimetric substrates. One-component systems include aromatic amines, aromatic alcohols, azines, and benzidines, such as tetramethyl benzidine-HCl. Suitable two-component systems include those in which one component is MBTH, an MBTH derivative (see for example those disclosed in U.S. patent application Ser. No. 08/302,575, incorporated herein by reference), or 4-aminoantipyrine and the other component is an aromatic amine, aromatic alcohol, conjugated amine, conjugated alcohol or aromatic or aliphatic aldehyde. Exemplary two-component systems are 3-methyl-2-benzothiazolinone hydrazone hydrochloride (MBTH) combined with 3-dimethylaminobenzoic acid (DMAB); MBTH combined with 3,5-dichloro-2-hydroxybenzene-sulfonic acid (DCHBS); and 3-methyl-2-benzothiazolinone hydrazone N-sulfonyl benzenesulfonate monosodium (MBTHSB) combined with 8-anilino-1 naphthalene sulfonic acid ammonium (ANS). In certain embodiments, the dye couple MBTHSB-ANS is preferred.

In yet other embodiments, signal producing systems that produce a fluorescent detectable product (or detectable non-fluorescent substance, e.g. in a fluorescent background) may be employed, such as those described in: Kiyoshi Zaitsu, Yosuke Ohkura: New fluorogenic substrates for Horseradish Peroxidase: rapid and sensitive assay for hydrogen peroxide and the Peroxidase. Analytical Biochemistry (1980) 109, 109–113.

As mentioned above, also of interest are signal producing systems that produce an electric current, e.g., as are employed in electrochemical test strips. Such reagents systems include redox reagent systems, which reagent systems provide for the species that is measured by the electrode and therefore is used to derive the concentration of analyte in a physiological sample. The redox reagent system present in the reaction area typically includes at least an enzyme(s) and a mediator. In many embodiments, the enzyme member(s) of the redox reagent system is an enzyme or plurality of enzymes that work in concert to oxidize the analyte of interest. In other words, the enzyme component of the redox reagent system is made up of a single analyte oxidizing enzyme or a collection of two or more enzymes that work in concert to oxidize the analyte of interest. Enzymes of interest include oxidases, dehydrogenases, lipases, kinases, diphorases, quinoproteins, and the like.

The specific enzyme present in the reaction area depends on the particular analyte for which the electrochemical test strip is designed to detect, where representative enzymes include: glucose oxidase, glucose dehydrogenase, cholesterol esterase, cholesterol oxidase, lipoprotein lipase, glycerol kinase, glycerol-3-phosphate oxidase, lactate oxidase, lactate dehydrogenase, pyruvate oxidase, alcohol oxidase, bilirubin oxidase, uricase, and the like. In many preferred embodiments where the analyte of interest is glucose, the enzyme component of the redox reagent system is a glucose oxidizing enzyme, e.g. a glucose oxidase or glucose dehydrogenase. The second component of the redox reagent system is a mediator component, which is made up of one or more mediator agents. A variety of different mediator agents are known in the art and include: ferricyanide, phenazine ethosulphate, phenazine methosulfate, phenylenediamine, 1-methoxy-phenazine methosulfate, 2,6-dimethyl-1,4-benzoquinone, 2,5-dichloro-1,4-benzoquinone, ferrocene derivatives, osmium bipyridyl complexes, ruthenium complexes, and the like. In those embodiments where glucose in the analyte of interest and glucose oxidase or glucose dehydrogenase are the enzyme components, mediators of particular interest are ferricyanide, and the like.

Other reagents that may be present in the reaction area include buffering agents, e.g. citraconate, citrate, malic, maleic, phosphate, "Good" buffers and the like. Yet other agents that may be present include: divalent cations such as calcium chloride, and magnesium chloride; pyrroloquinoline quinone; types of surfactants such as Triton, Macol, Tetronic, Silwet, Zonyl, and Pluronic; stabilizing agents such as albumin, sucrose, trehalose, mannitol, and lactose.

Depending upon the particular nature of the signal producing system, the system may or may not be associated with a support matrix material. In these embodiments, the porous matrix is an inert porous matrix and acts as a support for the various members of the signal producing system. A number of different porous matrices have been developed for use in various analyte detection assays, which matrices differ in terms of materials, pore sizes, dimensions and the like, where representative matrices include those described in U.S. patent application Ser. Nos.: 4,734,360; 4,900,666; 4,935,346; 5,059,394; 5,304,468; 5,306,623; 5,418,142; 5,426,032; 5,515,170; 5,526,120; 5,563,042; 5,620,863; 5,753,429; 5,573,452; 5,780,304; 5,789,255; 5,843,691; 5,846,486; 5,968,836 and 5,972,294; the disclosures of which are herein incorporated by reference. In principle, the nature of the porous matrix is not critical to the subject test strips and therefore is chosen with respect to other factors, including the nature of the instrument which is used to read the reagent test strip, convenience, type of assay to be performed with the reagent test strip, and the like.

As mentioned above, the reagent material, which may or may not include a supporting matrix as described above, is present on the reagent strip precursor as a narrow stripe that is positioned on one surface of the elongated support material and runs along the longitudinal axis of the support material. The width of the narrow reagent stripe may vary depending on the nature of the particular test strip being manufactured. In general the width of the narrow reagent stripe may range from about 0.05 to 0.50 inches, usually from about 0.10 to 0.4 inches and more usually from about 0.15 to 0.35 inches; where in certain embodiments the width of the narrow reagent stripe may range from about 0.10 to 0.50 inches, usually from about 0.15 to 0.4 inches and more usually from about 0.18 to 0.35 inches and in other embodiments the width of the narrow reagent stripe may range from about 0.05 to 0.30 inches, usually from about to 0.10 to 0.25 and more usually from about 0.15 to 0.20 inches.

The reagent strip precursor as described above may be produced using any convenient protocol. As such, the narrow reagent stripe can be laid down or attached to the support material along the central longitudinal axis, e.g., by joining two pieces, e.g., tapes, etc. A continuous process, e.g., one in which various rolls of material are brought together to produce the precursor (as is done in a continuous web process) or a discontinuous process, e.g., one in which the two strips are first cut and then joined to each other, may be employed. Other modes of strip precursor fabrication may also be employed.

The next step in the subject methods following provision of the reagent strip precursor, as described above, is to cut the precursor into a plurality of reagent test strips according to an inter-digitating pattern. By inter-digitating pattern is meant a pattern characterized by a series of inter-laced fingers or projections that are positioned along the narrow reagent stripe. A representative inter-digitating pattern is shown in FIG. 1. As can be seen in FIG. 1, the test strip precursor is in the form of a card 100 which has elongated support material 110 with a narrow reagent stripe 120 positioned along its central axis such that it is equidistant from each side, i.e., x and y are the same length. Superimposed on the card 100 is an inter-digitating pattern of test strips, which is characterized by a series of continuous and oppositely oriented fingers or projections along the reagent strip and center axis. The inter-digitating pattern shown in FIG. 1 is merely representative, where a number of inter-digitating patterns may be employed, as will be evident from the plurality of different test strip designs that are discussed infra.

Inter-digitating patterns employed in the subject methods are generally those that produce reagent test strips that include a sample region and a handling region, where the reagent material is located in the sample region. The respective areas of these two regions may vary, where the ratio of the areas of the two regions may range anywhere from about 0.05 to 0.95, usually from about 0.08 to 0.90 and more usually from about 0.10 to 0.92. Sample and handling regions are shown on the representative strips depicted in FIGS. 1–8, where a dashed line separates the two regions, e.g. the 140 handling region and the 150 sample region in strip shown in FIG. 1. In many embodiments, the area of the sample region may range from about 0.01 to 0.60 square inches, usually from about 0.015 to 0.50 square inches and more usually from about 0.03 to 0.45 square inches; where in certain embodiments the area of the sample region may range from about 0.10 to 0.60 square inches, usually from about 0.20 to 0.50 square inches and more usually from about 0.25 to 0.45 square inches and in other embodiments the area of the sample region may range from about 0.01 to 0.25 square inches usually from about 0.015 to 0.15 square inches and more usually from about 0.02 to 0.10 square inches. In many embodiments, the area of the holding region may range from about 0.02 to 0.80 square inches, usually from about 0.08 to 0.70 square inches and more usually from about 0.10 to 0.65 square inches; where in certain embodiments the area of the holding region may range from about 0.30 to 0.80 square inches, usually from about 0.40 to 0.70 square inches and more usually from about 0.45 to 0.65 square inches and in other embodiments the area of the holding region may range from about 0.02 to 0.30 square inches usually from about 0.08 to 0.25 square inches and more usually from about 0.10 to 0.20 square inches.

The ratio of the average width of the sample region to the average width of the handling region typically ranges from about 0.01 to 0.99, usually about 0.1 to 0.9 but is often about or is 0.5.

In other words, the inter-digitating pattern employed in the subject methods is generally one that provides for an aspect ratio of the sample region to handling/holding region ranges from about 0.1 to 0.9, where in certain embodiments an aspect ratio that is about 0.5 may be preferred. By aspect ratio is meant the ratio of the average width of the sample region to the average width of the holding domain, i.e., a to b in FIG. 1.

As described above, the test strip precursor is cut according to an inter-digitating pattern. In other words, the precursor is singulated into the individual test strips according to an inter-digitating pattern. By cut is meant either automated or manual cutting, i.e., the test strip blank may be manually cut or cut using an automated means into the plurality of reagent test strips, e.g., with a laser singulation means, a rotary die cutting means, etc. The inter-digitating pattern may be in the form of a guide, map, image or other direction means that directs or indicates how the test strip precursor should be cut into the reagent test strips. The pattern may or may not be visual on the test strip blank prior to cutting/singulation. Where the pattern is visible, the image may be apparent from a complete outline, a partial outline, or designated points or markings of a strip.

Reagent Test Strips

Also provided by the subject invention are reagent test strips that are produced by the subject methods in which a test strip precursor is cut according to an inter-digitating pattern, as described above. The reagent test strips of the subject invention generally include a sample domain and a handling or holding domain, where the sample domain includes the reagent material, which may or may not include a support matrix, as described above.

The size of the reagent test strips cut from the test strip precursor may vary. In many embodiments, the total area of a reagent test strip produced by the subject methods ranges from about 0.65 to 1.65 square inches, and usually from about 0.75 to 1.50 square inches. The length of a reagent test strip typically ranges from about 1.60 to 1.95 inches, and more typically from about 1.70 to 1.85. In many embodiments, them sample domain or region of the test strip has a hole located beneath the reagent material, so that a sample can be applied to one side of the reagent material and a color detected from the other side. In certain embodiments, the sections are joined together by a neck region, e.g., either expanded or constricted. Configurations that may find use in the present invention are configurations substantially the same as or identical to a reagent test strip selected from the group of configurations shown in FIGS. 2 to 8, which are now described in further detail.

Figure 2:
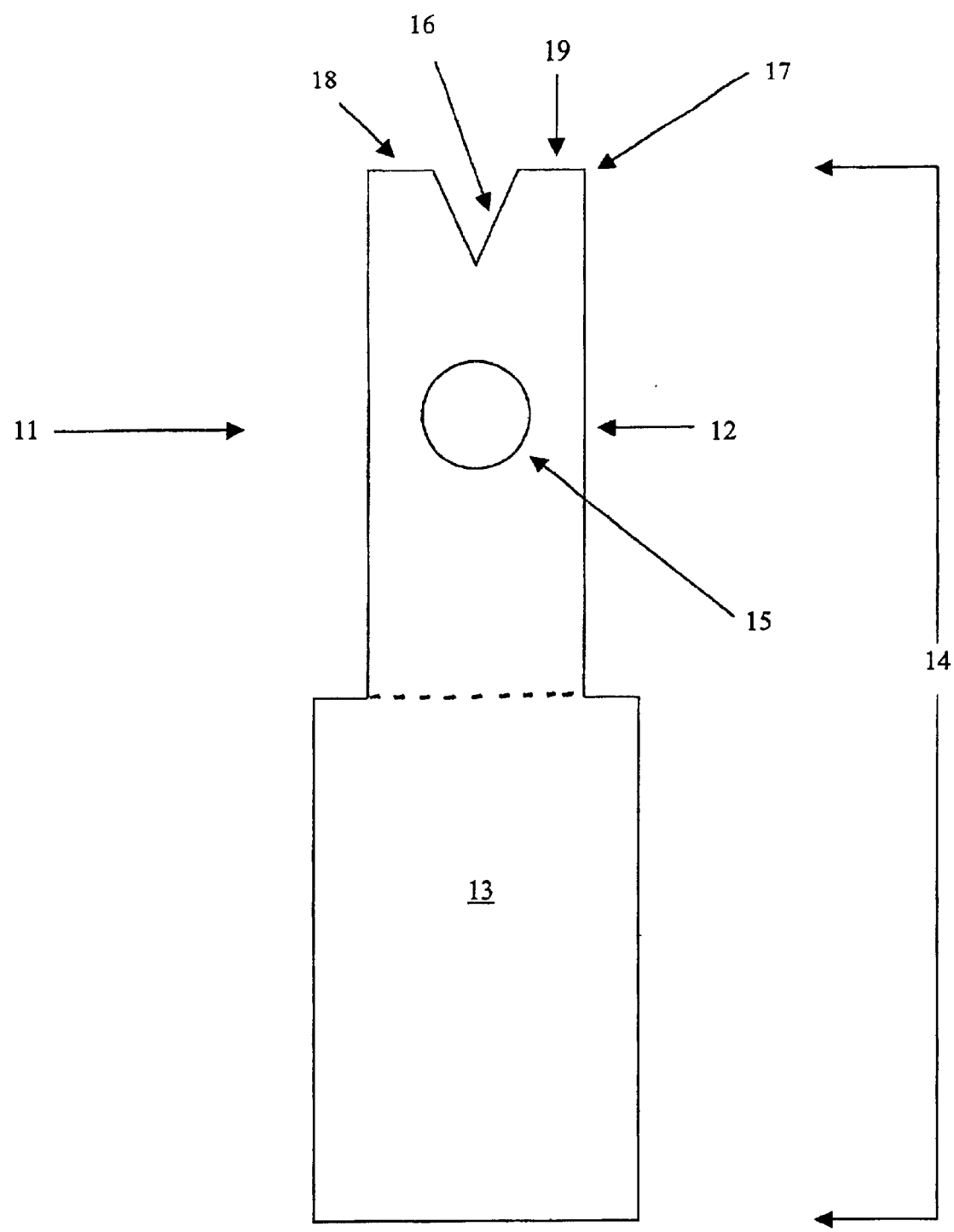
FIGS. 2 to 8 provide top view illustrations of various reagent test strip configurations.

FIG. 2 illustrates a top view of one embodiment of the reagent test strip. Reagent test strip 11 is comprised of two sections of differing size, a first or sample section 12 and a second or handling section 13. First section 12 is relatively smaller in size than second section 13, wherein second section 13 has an area ranging from about 0.50 to 0.75 square inches. The total area of reagent test strip 11 ranges from about 0.75 to 1.50 square inches and the total length 14 ranges from about 1.70 to 1.85 inches. Hole 15 is present in first section 12. Notch 16 is present on free edge 17 of first section 12, of which edges 18 and 19 are substantially straight.

Figure 3:
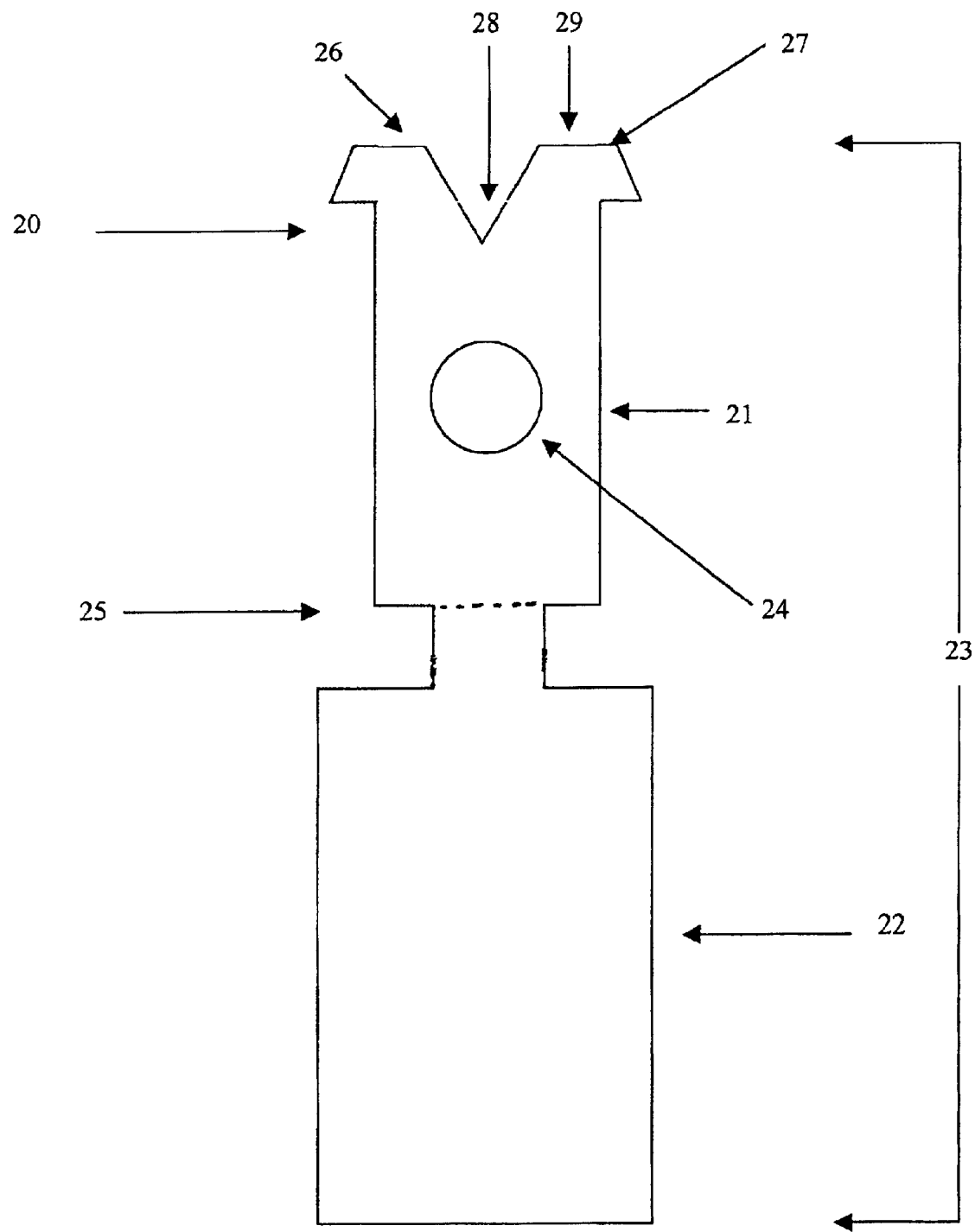

FIG. 3 illustrates a top view of another embodiment of the reagent test strip. Reagent test strip 20 is comprised of two sections of differing size, a first or sample section 21 and a second or handling section 22. First section 21 is relatively smaller in size than second section 22, wherein second section 22 has an area ranging from about 0.50 to 0.75 square inches. The total area of strip 20 ranges from about 0.75 to 1.50 square inches and the total length 23 ranges from about 1.70 to 1.85 inches. Hole 24 is present in first section 21. First section 21 is joined to second section 22 by constricted neck region 25. Lips 26 and 27 and notch 28 are on free edge 29 of first section 21.

Figure 4:
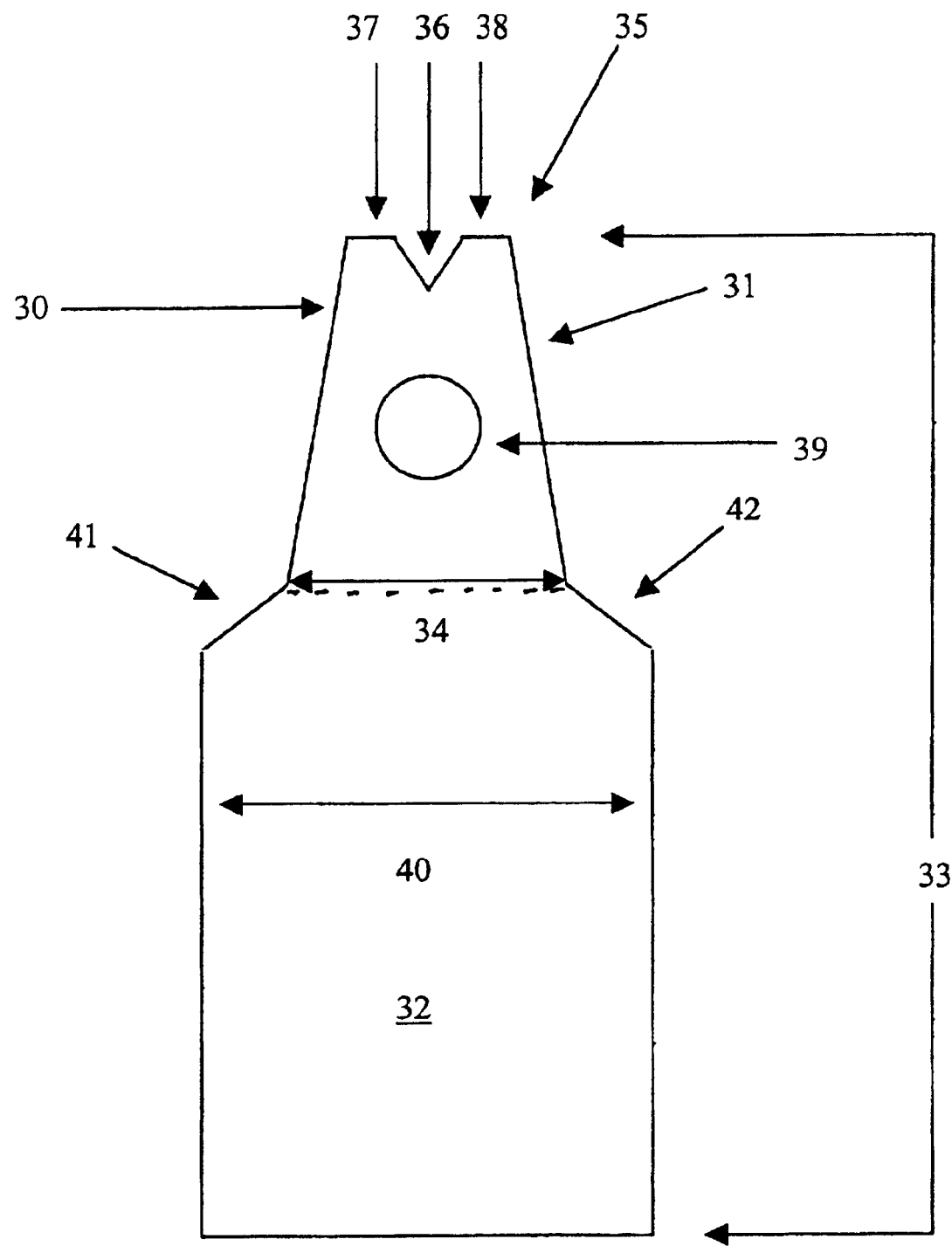

A further embodiment of the reagent test strip is illustrated in FIG. 4. Reagent test strip 30 is comprised of two sections of differing size, a first or sampling section 31 and a second or handling section 32. First section 31 is relatively smaller in size than second section 32, wherein second section 32 has an area ranging from about 0.50 to 0.75 square inches. The total area of strip 30 ranges from about 0.75 to 1.50 square inches and the total length 33 ranges from about 1.70 to 1.85 inches. First section 31 has a width 34, such that width 34 progressively narrows towards free edge 35 of first section 31. Free edge 35 has notch 36 therein, of which top edges 37 and 38 of notch 36 are substantially straight. Hole 39 is present in first section 31. Width 40 of second section 32 is slightly greater than width 34 of first section 31, thereby creating shoulders 41 and 42 where first section 31 joins second section 32.

Figure 5:
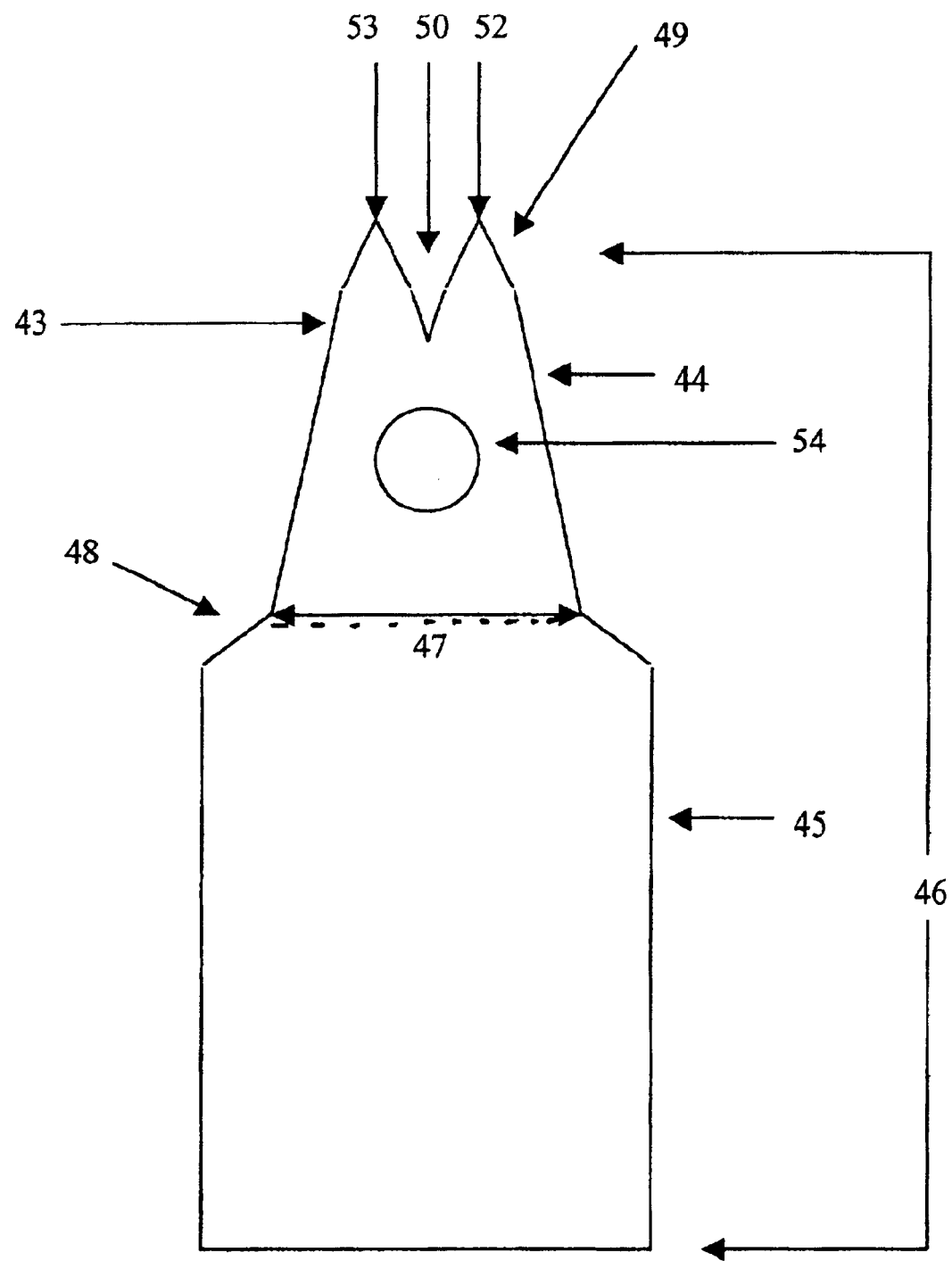

FIG. 5 illustrates a top view of a further embodiment of the reagent test strip. Reagent test strip 43 is comprised of two sections of differing size, a first sample section 44 and a second handling section 45. First section 44 is relatively smaller in size than second section 45, wherein second section 45 has an area ranging from about 0.50 to 0.75 square inches. The total area of strip 43 ranges from about 0.75 to 1.50 square inches and the total length 46 ranges from about 1.70 to 1.85 inches. Width 47 of first section 44 is greatest where first section 44 meets expanded neck region 48, and progressively narrows towards free edge 49 of first section 44. Free edge 49 of first section 44 has notch 50 therein, and is distally tapered, terminating in substantially pointed ends 52 and 53. Hole 54 is present in first section 44.

Figure 6:
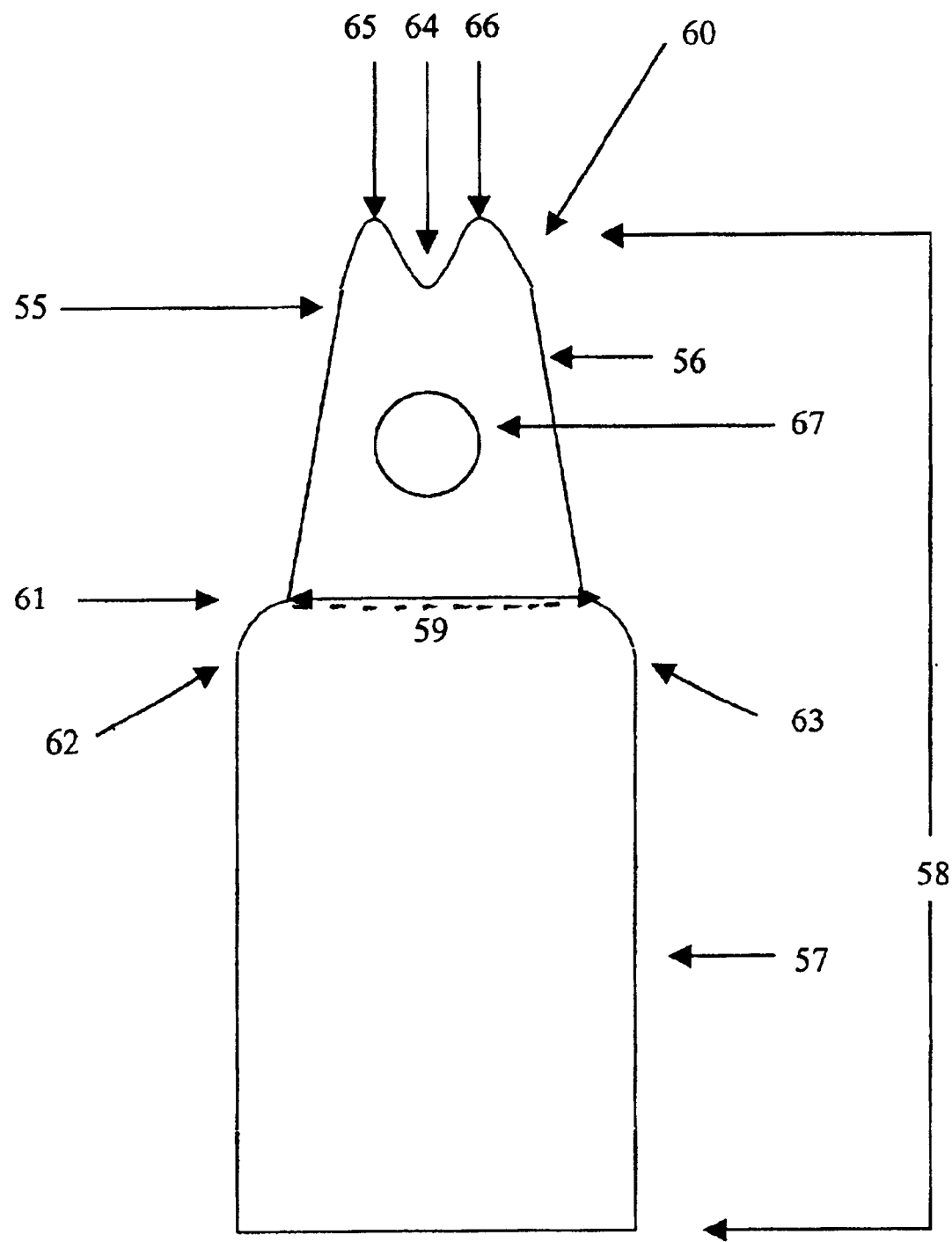

FIG. 6 illustrates a top view of reagent test strip 55. Reagent test strip 55 is characterized by having two sections of differing size, a first or sample section 56 and a second or handling section 57. First section 56 is relatively smaller in size than second section 57, wherein second section 57 has an area ranging from about 0.50 to 0.75 square inches. The total area of reagent test strip 55 ranges from about 0.75 to 1.50 square inches and the total length 58 ranges from about 1.70 to 1.85 inches. Width 59 of first section 56 is widest in the area where first section 56 is joined to second section 57, and progressively narrows towards free edge 60 of first section 56. First section 56 is joined to second section 57 by expanded neck region 61, creating rounded shoulders 62 and 63. Free edge 60 of first section 56 has notch 64 therein, of which top edges 65 and 66 are substantially rounded. Hole 67 is present in first section 56.

Figure 7:
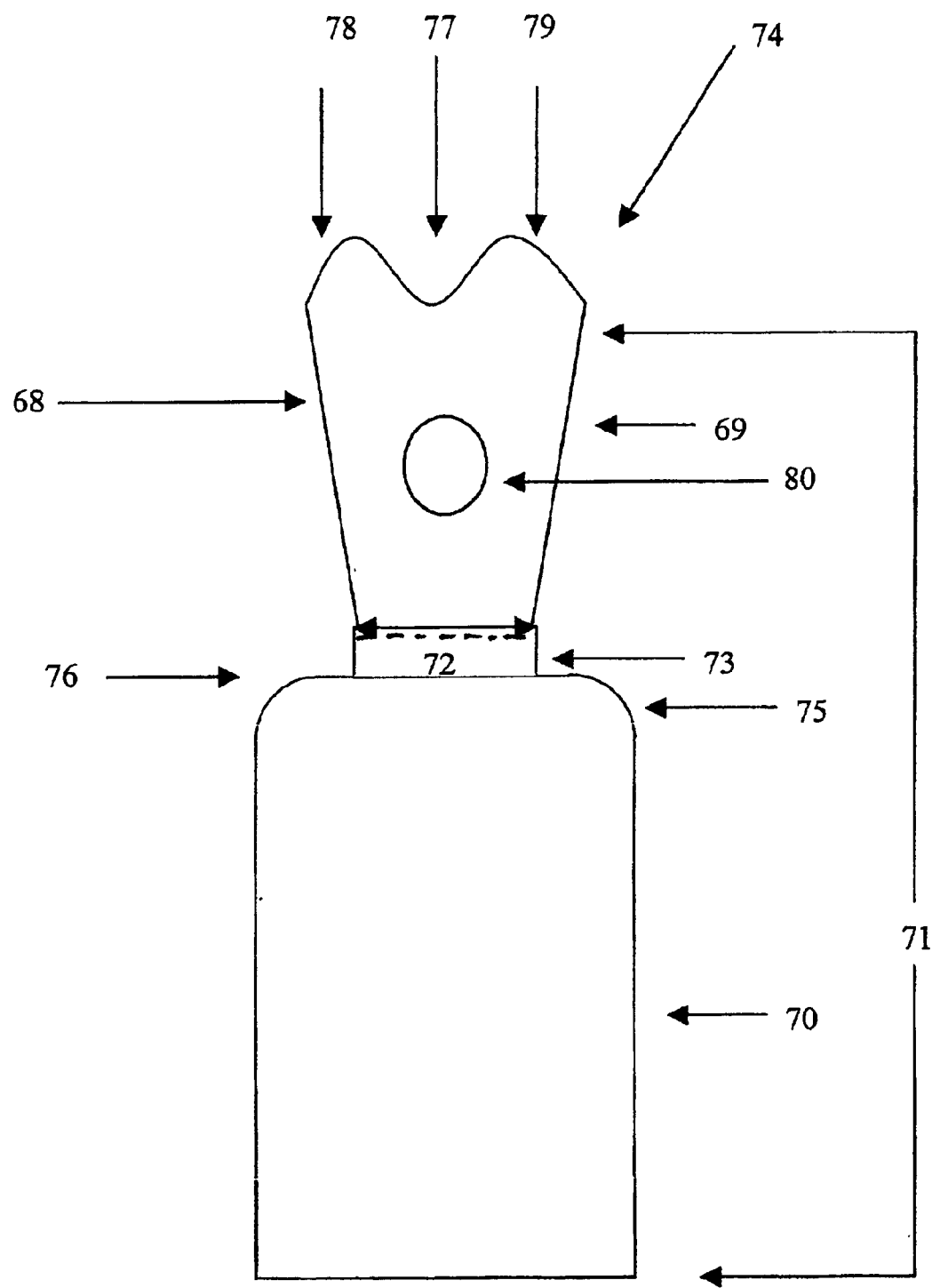

FIG. 7 illustrates a top view of another embodiment of the reagent test strip, reagent test strip 68. Reagent test strip 68 is characterized by having two sections of differing size, a first or sample section 69 and a second or handling section 70. First section 69 is relatively smaller in size than second section 70, wherein second section 70 has an area ranging from about 0.50 to 0.75 square inches. The total area of reagent test strip 68 ranges from about 0.75 to 1.50 square inches and the total length 71 ranges from about 1.70 to 1.85 inches. Width 72 of first section 69 is narrowest in the area where it meets neck region 73, and progressively widens towards free edge 74 of first section 69. First section 69 is joined to second section 70 by constricted neck region 73, where neck region 73 has substantially raised shoulders 75 and 76. Free edge 74 of first section 69 has a notch 77 therein, of which top edges 78 and 79 are substantially rounded. Hole 80 is present in first section 69.

Figure 8:
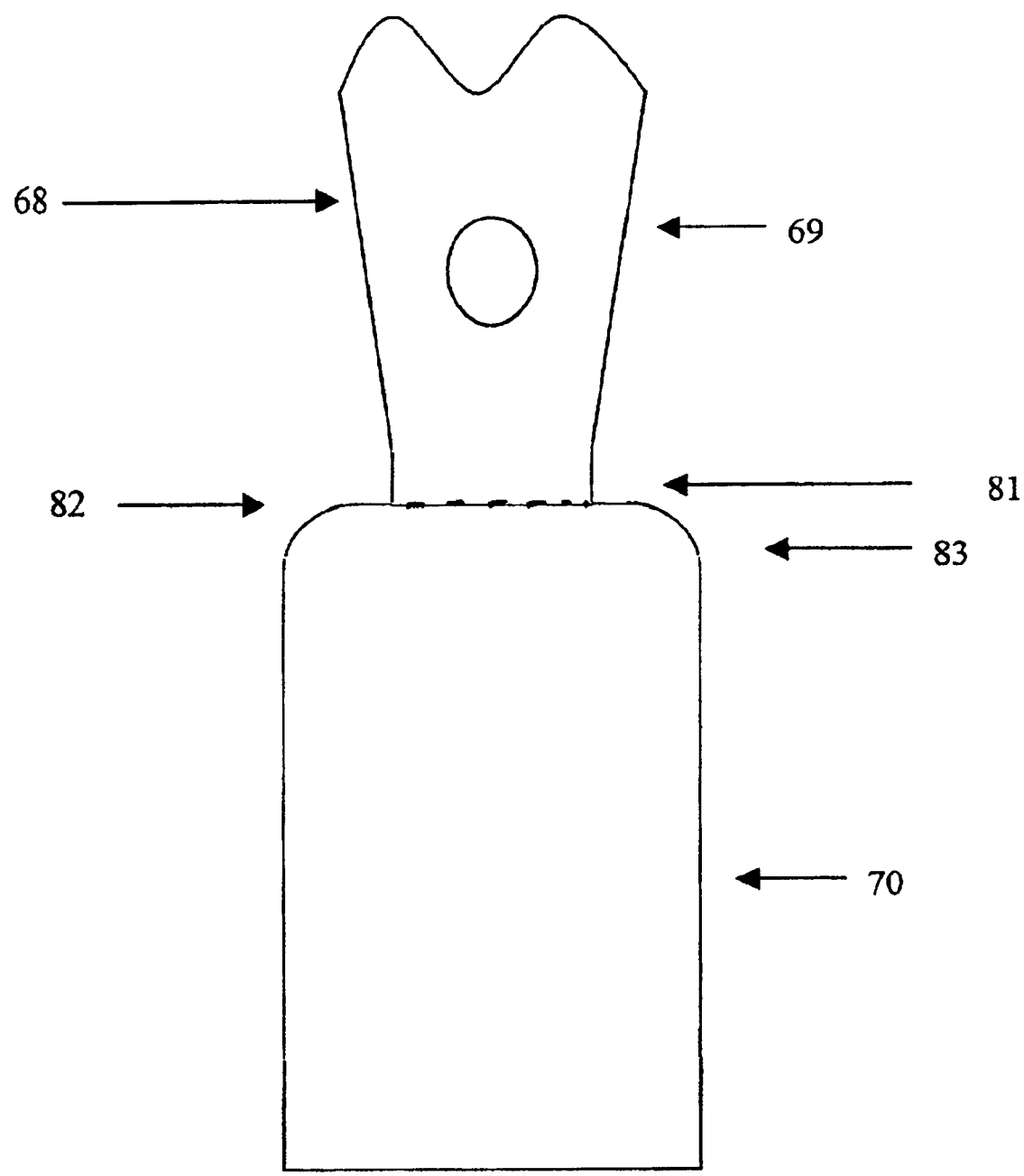

FIG. 8 illustrates reagent test strip 68 with first section 69 joined to second section 70 by constricted neck region 81, where neck region 81 has sloping shoulders 82 and 83.

In many embodiments of the subject methods, the reagent test strips produced by the subject methods can be employed with optical hand held meters. Of particular interest are optical hand held meters are described in U.S. Pat. Nos. 4,935,346; 5,304,468; 5,972,294; 5,179,005; 5,526,120; and 5,059,394, the disclosures of which are herein incorporated by reference. In many embodiments, the reagent strips produced by the subject methods can be read in a ONE TOUCH® meter as sold by Lifescan, Inc.

Methods of Use

Also provided by the subject invention are methods of using the subject reagent test strips to detect the presence of and/or determine the concentration of an analyte in a physiological sample. In these methods, the first step is to apply a sample suspected of containing the analyte of interest to the test strip, i.e., to the sample region of the test strip. Following the application of the sample to the test strip, the sample is allowed to react with the members of the signal producing system to produce a detectable product that is present in an amount proportional to the initial amount present in the sample. The amount of detectable product, e.g., signal produced by the signal producing system, is then determined and related to the amount of analyte in the initial sample. The detection and relation steps can be accomplished by either direct observation with the eye or with on optical instrument, e.g., an optical instrument that detects changes in reflectance. In certain embodiments, hand held optical instruments that suitably perform the above mentioned detection and relation steps are of interest, as described in U.S. Pat. Nos.: 4,935,346; 5,304,468; 5,972,294; 5,179,005; 5,526,120; 5,059,394; the disclosures of which are herein incorporated by reference, where a commercially available embodiment of such a meter is the ONE TOUCH® meter as sold by Lifescan, Inc.

A variety of different analytes may be detected using the subject reagent test strips, where representative analytes include glucose, cholesterol, lactate, alcohol, and the like. In many preferred embodiments, the subject methods are employed to determine the glucose concentration in a physiological sample. While in principle the subject methods may be used to determine the concentration of an analyte in a variety of different physiological samples, such as urine, tears, saliva, and the like, they are particularly suited for use in determining the concentration of an analyte in blood or blood fractions, e.g., blood derived samples, and more particularly in whole blood.

In practicing the subject methods, the first step is to apply a quantity of the physiological sample to the test strip, where the test strip is described supra. The amount of physiological sample, e.g., blood, that is applied to the test strip may vary, but generally ranges from about 0.2 $\mu$l to 40 $\mu$L, usually from 0.3 $\mu$L to 20 $\mu$L). Because of the nature of the subject test strip, where blood glucose concentration is of interest, the blood sample size that is applied to the test strip may be relatively small, ranging in size from about 2 $\mu$L to 40 $\mu$L, usually from about 5 $\mu$L to 20 $\mu$L. Where blood is the physiological sample, blood samples of a variety of hematocrits may be assayed with the subject methods, where the hematocrit may range from about 20% to 65%, usually from about 25% to 60%.

Following the application of the sample to the test strip, the sample is allowed to react with the members of the signal producing system to produce a detectable product that is present in an amount proportional to the initial amount present in the sample. The amount of detectable product, i.e., signal produced by the signal producing system, is then determined and related to the amount of analyte in the initial sample. The detection and relation steps can be accomplished by either direct observation with the eye or with a meter, e.g., described in U.S. patent application Ser. Nos.: 4,734,360; 4,900,666; 4,935,346; 5,059,394; 5,304,468; 5,306,623; 5,418,142; 5,426,032; 5,515,170; 5,526,120; 5,563,042; 5,620,863; 5,753,429; 5,573,452; 5,780,304; 5,789,255; 5,843,691; 5,846,486; 5,968,836 and 5,972,294; the disclosures of which are herein incorporated by reference.

Kits

Also provided by the subject invention are kits for use in practicing the subject invention. The kits of the subject invention at least include a reagent test strip, as described above. The subject kits may further include a means for obtaining a physiological sample. For example, where the physiological sample is blood, the subject kits may further include a means for obtaining a blood sample, such as a lance for sticking a finger, a lance actuation means, and the like. In addition, the subject kits may include a control solution or standard, e.g., a glucose control solution that contains a standardized concentration of glucose. In certain embodiments, the kits also include an optical instrument or meter, as described above, for detecting the amount of product produced on the strip following sample application and related the detected product to the amount of analyte in the sample, e.g., a ONE TOUCH® meter. Finally, the kits include instructions for using the subject reagent test strips in the determination of an analyte concentration in a physiological sample. These instructions may be present on one or more of the packaging, a label insert, containers present in the kits, and the like.

It is evident from the above discussion that the subject invention provides a highly efficient means of producing reagent test strips from a test strip blank. Using the subject methods, one can obtain a greater number of reagent test strips from a given amount of reagent material than can be achieved using previously known processes. Furthermore, the subject methods are adaptable to continuous web based processing protocols. As such, the subject invention represents a significant contribution to the art.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

All publications and patents cited in this specification are herein incorporated by reference as if each individual publication or patent were specifically and individually indicated to be incorporated by reference. The citation of any publication is for its disclosure prior to the filing date and should not be construed as an admission that the present invention is not entitled to antedate such publication by virtue of prior invention.

What is claimed is:

1. A method of manufacturing a plurality of reagent test strips, said method comprising:
   (a) providing a test strip precursor comprising an elongated support material having a planar surface and a stripe of reagent material positioned along a central axis thereof; and
   (b) cutting said test strip precursor into a plurality of reagent test strips according to an inter-digitating pattern comprising a series inter-laced, oppositely oriented projections positioned on said test strip precursor, wherein each of said strips produced includes a sample region and a handling region, where said reagent material is located in said sample region.

2. The method according to claim 1, wherein said test strip precursor is a continuous tape.

3. The method according to claim 1, wherein said test strip precursor is a card, wherein said card has a generally rectangular shape.

4. The method according to claim 1, wherein said method further comprises producing said test strip precursor.

5. The method according to claim 1, wherein said sample region includes a hole in said support material which is covered by said reagent material.

6. The method according to claim 1, wherein said sample region of said strip has an aspect ratio of about 0.5 relative to the handling region.

7. The method according to claim 1, wherein said test strips produced by said method can be used in a hand-held optical meter.

8. The reagent test strip according to claim 1, wherein said reagent test strip can be read by a hand held optical meter.

9. The method according to claim 1, wherein said reagent material comprises a signal producing system.

10. The method according to claim 9, wherein said signal producing system produces a color that can be related to the concentration of an analyte in a sample contacted with said reagent material.

11. The method according to claim 9, wherein said signal producing system produces an electrical current that can be related to the concentration of an analyte in a sample contacted with said reagent material.

12. A reagent test strip produced according to the method of claim 1, wherein said reagent test strip has a sample region and a handling region, wherein said reagent material is located in said sample region.

13. The reagent test strip according to claim 12, wherein said sample reagent of said test strip has an aspect ratio of that is about 0.5 relative to the handling region.

14. A method for determining the concentration of an analyte in a sample, said method comprising:
   (a) applying a fluid sample to a reagent test strip of claim 12;
   (b) detecting a signal from said reagent test strip; and
   (c) relating said detected signal to the concentration of analyte in said sample to determine the concentration of said analyte in said fluid sample.

15. The method according to claim 14, wherein said fluid sample is a biological sample.

16. The method according to claim 14, wherein said analyte is glucose.

17. The method according to claim 14, wherein said detecting and relating steps are performed by a hand held optical meter.

18. A kit for use in determining the concentration of an analyte in a physiological sample, said kit comprising:
   (a) a reagent test strip according to claim 12; and
   (b) at least one of:
      (i) a means for obtaining said physiological sample; and
      (ii) an analyte standard.

19. The kit according to claim 18, wherein said means for obtaining said physiological sample is a lance.

20. The kit according to claim 18, wherein said analyte standard comprises a standardized concentration of a known reagent.

21. The kit according to claim 18, wherein said kit comprises said means for obtaining said physiological sample and said analyte standard.

22. The kit according to claim 18, wherein said kit further comprises a hand held optical meter.

23. A method of manufacturing a plurality of reagent test strips, said method comprising;
   (a) providing a test strip precursor comprising an elongated support material having a planar surface and a stripe of reagent material positioned along a central axis thereof; and
   (b) cutting said test strip precursor into a plurality of reagent test strips according to an inter-digitating pattern comprising a series of inter-laced projections positioned on said test strip precursor representing test strips, each test strip comprising a sample region and a handling region and wherein said handling regions of adjacent test strips are positioned on opposite sides of said test strip precursor,
wherein each of said strips produced includes a sample region and a handling region, where said reagent material is located in said sample region.

* * * * *